United States Patent
Al Hares et al.

(10) Patent No.: US 9,387,083 B2
(45) Date of Patent: Jul. 12, 2016

(54) ACQUIRING AND UTILIZING KINEMATIC INFORMATION FOR PATIENT-ADAPTED IMPLANTS, TOOLS AND SURGICAL PROCEDURES

(71) Applicant: CONFORMIS, INC., Bedford, MA (US)

(72) Inventors: Ghaith Al Hares, Aachen (DE); Klaus Radermacher, Aachen (DE)

( * ) Notice: Subject to any disclaimer, the term of this patent is extended or adjusted under 35 U.S.C. 154(b) by 0 days.

(21) Appl. No.: 14/168,947

(22) Filed: Jan. 30, 2014

(65) Prior Publication Data

US 2014/0222157 A1 Aug. 7, 2014

Related U.S. Application Data

(60) Provisional application No. 61/758,755, filed on Jan. 30, 2013.

(51) Int. Cl.
  *A61F 2/38* (2006.01)
  *A61F 2/30* (2006.01)
  *A61F 2/46* (2006.01)

(52) U.S. Cl.
  CPC .............. *A61F 2/30942* (2013.01); *A61F 2/38* (2013.01); *A61F 2002/30952* (2013.01); *A61F 2002/4658* (2013.01); *A61F 2002/4668* (2013.01)

(58) Field of Classification Search
  None
  See application file for complete search history.

(56) References Cited

U.S. PATENT DOCUMENTS

| | | | |
|---|---|---|---|
| 4,813,436 A | 3/1989 | Au | 128/779 |
| 4,822,365 A | 4/1989 | Walker et al. | 623/20 |
| 4,823,807 A | 4/1989 | Russell et al. | 128/773 |
| 4,841,975 A | 6/1989 | Woolson | 128/653 |
| 4,936,862 A | 6/1990 | Walker et al. | 623/23 |
| 5,007,936 A | 4/1991 | Woolson | 623/23 |
| 5,099,859 A | 3/1992 | Bell | 128/781 |
| 5,129,908 A | 7/1992 | Petersen | 606/88 |
| 5,274,565 A | 12/1993 | Reuben | 364/474.24 |
| 5,326,363 A | 7/1994 | Aikins | 623/20 |
| 5,445,152 A | 8/1995 | Bell et al. | 128/653.5 |
| 5,541,515 A | 7/1996 | Tsujita | 324/318 |
| 5,682,886 A | 11/1997 | Delp et al. | 128/653.1 |
| 5,741,215 A | 4/1998 | D'Urso | 600/407 |
| 5,768,134 A | 6/1998 | Swaelens et al. | 364/468.28 |

(Continued)

FOREIGN PATENT DOCUMENTS

| | | | | |
|---|---|---|---|---|
| CN | 1480111 A | 3/2004 | | A61F 2/30 |
| DE | 4434539 C2 | 4/1996 | | A61F 2/38 |

(Continued)

OTHER PUBLICATIONS

International Searching Authority, International Search Report—International Application No. PCT/US2013/036506 dated Jul. 16, 2013, together with the Written Opinion of the International Searching Authority, 10 pages.

(Continued)

*Primary Examiner* — Jason-Dennis Stewart
(74) *Attorney, Agent, or Firm* — Sunstein Kann Murphy & Timbers LLP (57) ABSTRACT

Various embodiments of methods for obtaining kinematic information regarding a joint, including information regarding the joint in a weight-bearing position, are disclosed, as well as methods of designing implants, instruments, and surgical repair systems based on the kinematic information.

14 Claims, 6 Drawing Sheets

(56) References Cited

U.S. PATENT DOCUMENTS

| | | | | |
|---|---|---|---|---|
| 5,772,595 | A | 6/1998 | Votruba et al. | 600/415 |
| 5,810,006 | A | 9/1998 | Votruba et al. | 128/653.2 |
| 5,899,859 | A | 5/1999 | Votruba et al. | 600/415 |
| 6,126,690 | A | 10/2000 | Ateshian et al. | 623/18 |
| 6,161,080 | A | 12/2000 | Aouni-Ateshian et al. | 703/11 |
| 6,254,639 | B1 | 7/2001 | Peckitt | 623/11.11 |
| 6,459,948 | B1 | 10/2002 | Ateshian et al. | 700/117 |
| 6,482,209 | B1 | 11/2002 | Engh et al. | 606/79 |
| 6,510,334 | B1 | 1/2003 | Schuster et al. | 600/407 |
| 6,712,856 | B1 | 3/2004 | Carignan et al. | 623/20.35 |
| 6,932,842 | B1 | 8/2005 | Litschko et al. | 623/16.11 |
| 6,978,188 | B1 | 12/2005 | Christensen | 700/118 |
| 7,239,908 | B1 | 7/2007 | Alexander et al. | 600/427 |
| 7,468,075 | B2 | 12/2008 | Lang et al. | 623/16.11 |
| 7,603,192 | B2 | 10/2009 | Martin et al. | 700/98 |
| 7,611,519 | B2 | 11/2009 | Lefevre et al. | 606/102 |
| 7,881,768 | B2 | 2/2011 | Lang et al. | 600/407 |
| 7,983,777 | B2 | 7/2011 | Melton et al. | 700/98 |
| 8,036,729 | B2 | 10/2011 | Lang et al. | 600/407 |
| 8,086,336 | B2 | 12/2011 | Christensen | 700/98 |
| 8,112,142 | B2 | 2/2012 | Alexander et al. | 600/407 |
| RE43,282 | E | 3/2012 | Alexander et al. | 600/427 |
| 8,211,181 | B2 | 7/2012 | Walker | 623/20.21 |
| 8,234,097 | B2 | 7/2012 | Steines et al. | 703/1 |
| 8,306,601 | B2 | 11/2012 | Lang et al. | 600/407 |
| 8,337,507 | B2 | 12/2012 | Lang et al. | 606/102 |
| 8,343,218 | B2 | 1/2013 | Lang et al. | 623/16.11 |
| 8,352,056 | B2 | 1/2013 | Lee et al. | 700/97 |
| 8,369,926 | B2 | 2/2013 | Lang et al. | 600/407 |
| 8,377,073 | B2 | 2/2013 | Wasielewski | 606/102 |
| 8,380,471 | B2 | 2/2013 | Iannotti et al. | 703/6 |
| 8,407,067 | B2 | 3/2013 | Uthgenannt et al. | 705/2 |
| 8,457,930 | B2 | 6/2013 | Schroeder | 703/1 |
| 8,473,305 | B2 | 6/2013 | Belcher et al. | 705/2 |
| 8,480,754 | B2 | 7/2013 | Bojarski et al. | 623/20.35 |
| 8,486,150 | B2 | 7/2013 | White et al. | 623/20.21 |
| 8,521,492 | B2 | 8/2013 | Otto et al. | 703/6 |
| 8,532,807 | B2 | 9/2013 | Metzger | 700/98 |
| 8,545,569 | B2 | 10/2013 | Fitz et al. | 623/20.14 |
| 8,556,983 | B2 | 10/2013 | Bojarski et al. | 623/20.35 |
| 8,617,242 | B2 | 12/2013 | Philipp | 623/16.11 |
| 8,623,026 | B2 | 1/2014 | Wong et al. | 606/96 |
| 8,634,617 | B2 | 1/2014 | Tsougarakis et al. | 382/128 |
| 8,638,998 | B2 | 1/2014 | Steines et al. | 382/128 |
| 8,690,945 | B2 | 4/2014 | Fitz et al. | 623/16.11 |
| 8,709,089 | B2 | 4/2014 | Lang et al. | 623/18.11 |
| 8,735,773 | B2 | 5/2014 | Lang | 219/121.72 |
| 8,771,365 | B2 | 7/2014 | Bojarski et al. | 623/20.32 |
| 8,906,107 | B2 | 12/2014 | Bojarski et al. | 623/20.35 |
| 9,180,015 | B2 | 11/2015 | Fitz et al. | 382/128 |
| 9,186,254 | B2 | 11/2015 | Fitz et al. | |
| 2002/0052606 | A1 | 5/2002 | Bonutti | 606/88 |
| 2002/0059049 | A1 | 5/2002 | Bradbury et al. | 703/11 |
| 2002/0072821 | A1 | 6/2002 | Baker | 700/98 |
| 2002/0087274 | A1 | 7/2002 | Alexander et al. | 702/19 |
| 2003/0055502 | A1 | 3/2003 | Lang et al. | 623/16.11 |
| 2003/0216669 | A1 | 11/2003 | Lang et al. | 600/587 |
| 2003/0236473 | A1* | 12/2003 | Dore et al. | 600/587 |
| 2004/0102866 | A1 | 5/2004 | Harris et al. | 700/117 |
| 2004/0117015 | A1 | 6/2004 | Biscup | 623/16.11 |
| 2005/0148843 | A1 | 7/2005 | Roose | 600/407 |
| 2005/0197814 | A1 | 9/2005 | Aram et al. | 703/11 |
| 2005/0216305 | A1 | 9/2005 | Funderud | 705/2 |
| 2006/0094951 | A1 | 5/2006 | Dean et al. | 600/407 |
| 2006/0136058 | A1 | 6/2006 | Pietrzak | 623/13.14 |
| 2006/0149283 | A1 | 7/2006 | May et al. | 606/96 |
| 2007/0118055 | A1 | 5/2007 | McCombs | 600/587 |
| 2007/0118243 | A1 | 5/2007 | Schroeder et al. | 700/117 |
| 2007/0255288 | A1 | 11/2007 | Mahfouz et al. | 606/102 |
| 2007/0276501 | A1 | 11/2007 | Betz et al. | 623/17.16 |
| 2008/0058945 | A1 | 3/2008 | Hajaj et al. | 623/20.14 |
| 2008/0119940 | A1 | 5/2008 | Otto et al. | 623/20.31 |
| 2008/0172125 | A1 | 7/2008 | Ek | 623/14.12 |
| 2008/0215059 | A1 | 9/2008 | Carignan et al. | 606/96 |
| 2008/0255445 | A1 | 10/2008 | Neubauer et al. | 600/416 |
| 2008/0257363 | A1 | 10/2008 | Schoenefeld et al. | 128/897 |
| 2008/0262624 | A1 | 10/2008 | White et al. | 623/20.32 |
| 2009/0149977 | A1 | 6/2009 | Schendel | 700/98 |
| 2009/0151736 | A1 | 6/2009 | Belcher et al. | 128/898 |
| 2009/0226068 | A1 | 9/2009 | Fitz et al. | 382/131 |
| 2009/0270868 | A1 | 10/2009 | Park et al. | 606/87 |
| 2010/0292963 | A1 | 11/2010 | Schroeder | 703/1 |
| 2010/0332194 | A1 | 12/2010 | McGuan et al. | 703/1 |
| 2011/0046735 | A1 | 2/2011 | Metzger et al. | 623/14.12 |
| 2011/0087465 | A1 | 4/2011 | Mahfouz | 703/1 |
| 2011/0092804 | A1 | 4/2011 | Schoenefeld et al. | 600/416 |
| 2011/0093108 | A1 | 4/2011 | Ashby et al. | 700/103 |
| 2011/0184526 | A1 | 7/2011 | White et al. | 623/20.32 |
| 2011/0305379 | A1 | 12/2011 | Mahfouz | 382/131 |
| 2012/0041446 | A1 | 2/2012 | Wong et al. | 606/96 |
| 2012/0116203 | A1 | 5/2012 | Vancraen et al. | 600/407 |
| 2012/0191420 | A1 | 7/2012 | Bojarski et al. | 703/1 |
| 2012/0209394 | A1 | 8/2012 | Bojarski et al. | 623/20.32 |
| 2012/0265496 | A1 | 10/2012 | Mahfouz | 703/1 |
| 2012/0310364 | A1 | 12/2012 | Li et al. | 623/23.55 |
| 2013/0006598 | A1 | 1/2013 | Alexander et al. | 703/11 |
| 2013/0035766 | A1 | 2/2013 | Meridew | 623/22.21 |
| 2013/0158671 | A1 | 6/2013 | Uthgenannt et al. | 623/20.35 |
| 2013/0199259 | A1 | 8/2013 | Smith | 72/362 |
| 2013/0203031 | A1 | 8/2013 | Mckinnon et al. | 434/262 |
| 2013/0317511 | A1 | 11/2013 | Bojarski et al. | 606/102 |
| 2015/0057756 | A1 | 2/2015 | Lang et al. | 623/20.15 |

FOREIGN PATENT DOCUMENTS

| | | | | |
|---|---|---|---|---|
| EP | 0704193 | A1 | 4/1996 | A61F 2/30 |
| EP | 1074229 | A2 | 2/2001 | A61F 2/38 |
| WO | WO 95/28688 | A1 | 10/1995 | G06T 15/00 |
| WO | WO 00/35346 | A2 | 6/2000 | A61B 5/11 |
| WO | WO 00/68749 | A1 | 11/2000 | G05B 19/4099 |
| WO | WO 01/70142 | A1 | 9/2001 | A61F 2/38 |
| WO | WO 02/22013 | A2 | 3/2002 | A61B 5/055 |
| WO | WO 02/22014 | A1 | 3/2002 | A61B 5/055 |
| WO | WO 2006/092600 | A1 | 9/2006 | A61B 19/00 |
| WO | WO 2008/021494 | A2 | 2/2008 | G06F 19/00 |
| WO | WO 2010/099353 | A1 | 9/2010 | A61F 2/30 |
| WO | WO 2010/099359 | A1 | 9/2010 | A61F 2/00 |
| WO | WO 2010/121147 | | 10/2010 | A61B 17/90 |
| WO | WO 2012/021894 | A2 | 2/2012 | A61F 2/46 |
| WO | WO 2012/027150 | A2 | 3/2012 | G06F 19/00 |
| WO | WO 2013/062850 | A1 | 5/2013 | A61F 2/30 |
| WO | WO 2013/155501 | | 10/2013 | A61F 2/30 |

OTHER PUBLICATIONS

Alexander et al., "Correcting for Deformation in Skin-Based Marker Systems," Proceedings of the 3rd Annual Gait and Clinical Movement Analysis Meeting San Diego, CA, pp. 355-361, 2001.

Alexander et al., "Internal to External Correspondence in the Analysis of Lower Limb Bone Motion," Proceedings of the 1999 ASME Summer Bioengineering Conference Big Sky Montana, 2 pages, 1999.

Alexander et al., "State Estimation Theory in Human Movement Analysis," Proceedings of the 1998 ASME International Mechanical Engineering Congress 2 pages, 1998.

Alexander, "Estimating the Motion of Bones From Markers on the Skin," Doctoral Dissertation University of Illinois at Chicago, pp. 1-111, 1998.

Alexander et al., "Dynamic Functional Imaging of the Musculoskeletal System," ASME Winter International Congress and Exposition Nashville TN, 2 pages, 1999.

Andriacchi et al., "Gait Analysis As a Tool to Assess Joint Kinetics," Biomechanics of Normal and Pathological Human Articulating Joints Nijhoff, Series E: Applied Sciences, No. 93, pp. 83-102, 1985.

Andriacchi et al., "In Vivo Measurement of Six-Degrees-OfFreedom Knee Movement During Functional Testing," Transactions of the Orthopedic Research Society, p. 698, Feb. 13-16, 1995.

Andriacchi et al., "A Point Cluster Method for in Vivo Motion Analysis: Applied to a Study of Knee Kinematics," Journal of Biomechanical Engineering, vol. 120, No. 12, pp. 743-749, Dec. 1998.

Andriacchi, "Dynamics of Knee Malalignment," Orthopedic Clinics of North America, vol. 25, No. 3, pp. 395-403, Jul. 1994.

(56) References Cited

OTHER PUBLICATIONS

Blazina et al., "Patellofemoral Replacement: Utilizing a Customized Femoral Groove Replacement," vol. 5, Issue 1, pp. 53-55, 1990.
Cohen et al., "Computer-Aided Planning of Patellofemoral Joint OA Surgery: Developing Physical Models from Patient MRI," MICCAI, 13 pages, Oct. 11-13, 1998.
Cohen et al., "Knee Cartilage Topography, Thickness, and Contact Areas from MRI: in-Vitro Calibration and in-Vivo Measurements," Osteoarthritis and Cartilage, vol. 7, No. 1, pp. 95-109, 1999.
Delp et al., "Computer Assisted Knee Replacement," Clinical Orthopaedics, vol. 354, pp. 49-56, Sep. 1998.
Delp et al., "A Graphics-Based Software System to Develop and Analyze Models of Musculoskeletal Structures," Comput. Biol. Med., vol. 25, No. 1, pp. 21-34, 1995.
Harrysson et al., "Custom-Designed Orthopedic Implants Evaluated Using Finite Element Analysis of Patient-Specific Computed Tomography Data: Femoral-Component Case Study," BMC Musculoskeletal Disorders, vol. 8, No. 91, 10 pages, Sep. 13, 2007.
Johnson et al., "The Distribution of Load Across The Knee—A Comparison of Static and Dynamic Measurements," Journal of Bone and Joint Surgery, vol. 62B, pp. 346-349, 1980.
Johnson, "In-Vivo Contact Kinematics of The Knee Joint: Advancing the Point Cluster Technique," Ph.D. Thesis University of Minnesota, 225 pages, 1999.
Jonsson et al., "Precision of Hyaline Cartilage Thickness Measurements," Acta Radiol vol. 33, No. 3, pp. 234-239, 1992.
Kidder et al., "3-D Model Acquisition, Design, Planning and Manufacturing of Orthopaedic Devices: A Framework," Proceedings of the SPIE Advanced Sensor and Control-System Interface Boston MA vol. 2911, pp. 9-22, Nov. 1996.
Lafortune et al., "Three Dimensional Kinematics of the Human Knee During Walking," J. of Biomechanics vol. 25, No. 4, pp. 347-357, 1992.
Lang et al., "Functional Joint Imaging: A New Technique Integrating MRI and Biomotion Studies," International Society for Magnetic Resonance in Medicine Denver, 1 page, Apr. 18-24, 2000.
Lombardi et al., "Patient-Specific Approach in Total Knee Arthroplasty," Orthopedics, vol. 31, Issue 9, 8 pages, Sep. 2008.
Lu et al., "Bone Position Estimation from Skin Marker Coordinates Using Global Optimization with Joint Constraints," Journal of Biomechanics, vol. 32, pp. 129-134, 1999.
Lucchetti et al., "Skin Movement Artefact Assessment and Compensation in the Estimation of Knee-Joint Kinematics," Journal of Biomechanics, vol. 31, pp. 977-984, 1998.
Radin et al. "Characteristics of Joint Loading as it Applies to Osteoarthrosis," Mow VC Woo S.Y. Ratcliffe T. eds. Symposium on Biomechanics of Diarthrodial Joints, New York NY: Springer-Verlag, vol. 2, pp. 437-451, 1990.
Thoma et al. In German: "Custom-Made Knee Endoprosthetics Using Subtraction Data of Three-Dimensional CT Scans—A New Approach," Der Orthopäde, Springer-Verlag, vol. 29, No. 7, pp. 641-644, Jul. 2000.
Thoma et al., English Translation with Certification: "Custom-Made Knee Endoprosthetics Using Subtraction Data of Three-Dimensional CT Scans—A New Approach," Der Orthopäde, Springer-Verlag, vol. 29, No. 7, pp. 641-644, Jul. 2000.
Thoma et al., In German: "Use of a New Subtraction Procedure Based on Three-Dimensional CT Scans for the Individual Treatment of Bone Defects in the Hip and Knee," Journal DGPW, No. 17, pp. 27-28, May 1999.
Thoma et al., English Translation with Certification: "Use of a New Subtraction Procedure Based on Three-Dimensional CT Scans for the Individual Treatment of Bone Defects in the Hip and Knee," Journal DGPW, No. 17, pp. 27-28, May 1999.
International Searching Authority, International Search Report—International Application No. PCT/US2014/030001 dated Aug. 27, 2014, together with the Written Opinion of the International Searching Authority, 10 pages.

* cited by examiner

ACQUIRING AND UTILIZING KINEMATIC INFORMATION FOR PATIENT-ADAPTED IMPLANTS, TOOLS AND SURGICAL PROCEDURES

RELATED APPLICATIONS

This application claims the benefit of U.S. Provisional Application No. 61/758,755, entitled "Imaging, Modeling, Analyzing and Using Anatomical Data for Patient-Adapted Implants, Designs, Tools and Surgical Procedures" and filed Jan. 30, 2013, the disclosure of which is incorporated herein by reference in its entirety.

TECHNICAL FIELD

The present disclosure relates to articular repair systems (e.g., resection cut strategy, guide tools, and implant components) as described in, for example, U.S. patent application Ser. No. 13/397,457, entitled "Patient-Adapted and Improved Orthopedic Implants, Designs And Related Tools," filed Feb. 15, 2012, and published as U.S. Patent Publication No. 2012-0209394, which is incorporated herein by reference in its entirety. In particular, various embodiments disclosed herein relate to determining kinematic information for use in articular repair systems.

DETAILED DESCRIPTION

Various embodiments described herein include the use of automated, and/or semi-automated computing systems to obtain, quantify, classify and/or model patient anatomical information for use in selecting and/or designing surgical tools, implants and/or surgical procedures to repair and/or replace portions of a patient's anatomy. The models created can include actual and/or approximate models of the patient's existing anatomy as well as models of optimal, desired, undesired and/or unacceptable anatomy derived using, at least in part, the patient's existing anatomical data. The derived models can be created using a wide variety of tools, techniques and/or data sources.

The image data, derived models and/or actual models can be utilized to select, design and/or manufacture surgical tools, implants and surgical techniques that, when utilized on the patient, create an optimal and/or otherwise acceptable repair and/or replacement of the relevant patient anatomy. These models will also desirably facilitate the creation of highly durable implant components that can be easily implanted using less invasive and/or least invasive surgical techniques.

In some embodiments, an initial step in repairing and/or replacing one or more anatomical features of a patient can be to assess the size, shape and/or condition of the relevant patient anatomy. For an orthopedic implant, this process typically includes obtaining one or more images of the patient's joint and/or other relevant patient anatomy (e.g., adjacent anatomical areas and/or other features of interest) using, for example, non-invasive imaging modalities (as well as other imaging and/or anatomical derivation techniques known in the art). The raw electronic image data can be used to create one or more representations or "models" of the patient's anatomy. These representations can include electronic models as well as 2-Dimensional images and/or 3-Dimensional physical reproductions of the patient anatomy.

In various embodiments, the models can be used to select and/or design an orthopedic implant appropriate for the patient's anatomy. In other embodiments, the models can be processed and/or modified to generate one or more modified versions of the patient anatomy, including portions of a joint and/or surfaces within or adjacent to the joint, with the derived model(s) representing desired (and/or undesired) conditions of the joint at various stages, including after surgical repair and/or replacement. In various embodiments, the raw image data can be used to create models that can be used to analyze the patient's existing joint structure and kinematics, and to devise and evaluate a course of corrective action, including surgical implants, tools, and/or procedures.

In some embodiments, the data and/or models can be used to design an implant having one or more patient-specific features, such as a surface or curvature. Additionally or alternatively, the various models described herein can be utilized to plan a surgical procedure as well as to design and/or select surgical tools useful during the procedure. In various embodiments, the models can be optimized or otherwise modified using a wide variety of techniques and/or data sources, to create one or more desired models that represent one or more desired "improvements" or outcomes of a surgical repair and/or replacement procedure.

Figure 1:
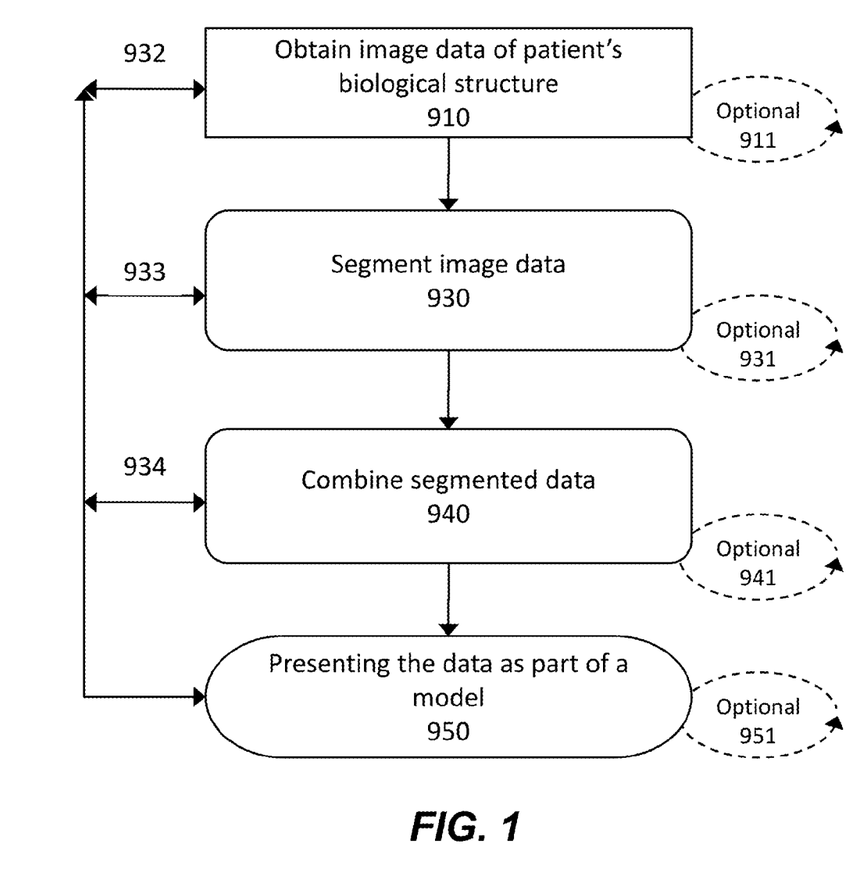
FIG. 1 is a flow chart illustrating an exemplary process for generating a model of a patient's joint.

One initial step in many embodiments is to obtain image data of a patient's anatomy. As illustrated in FIG. 1, a method of generating a model of a patient's joint or other biological feature can include one or more of the steps of obtaining image data of a patient's biological structure 910; analyzing or segmenting the image data 930; combining the segmented data 940; and presenting the data as part of a model 950.

Image data can be obtained 910 from near or within the patient's biological structure(s) of interest. For example, pixel or voxel data from one or more radiographic or tomographic images of a patient's joint can be obtained, for example, using computed or magnetic resonance tomography. A wide variety of imaging modalities known in the art can be used, including X-ray, ultrasound, laser imaging, MRI, PET, SPECT, radiography including digital radiography, digital tomosynthesis, cone beam CT, and contrast enhanced imaging. Image data can also include electronic image data derived from physical image "films" or "plates" through scanning or other capture techniques.

The one or more pixels or voxels (as well as other electronic values representing the image data) can be converted into one or a set of values. For example, a single pixel/voxel or a group of pixels/voxels can be converted to coordinate values, e.g., a point in a 2D or 3D coordinate system. The set of values also can include a value corresponding to the pixel/ voxel intensity or relative grayscale color. Moreover, the set of values can include information about neighboring pixels or voxels, for example, information corresponding to relative intensity or grayscale color and or information corresponding to relative position.

Figure 2A:
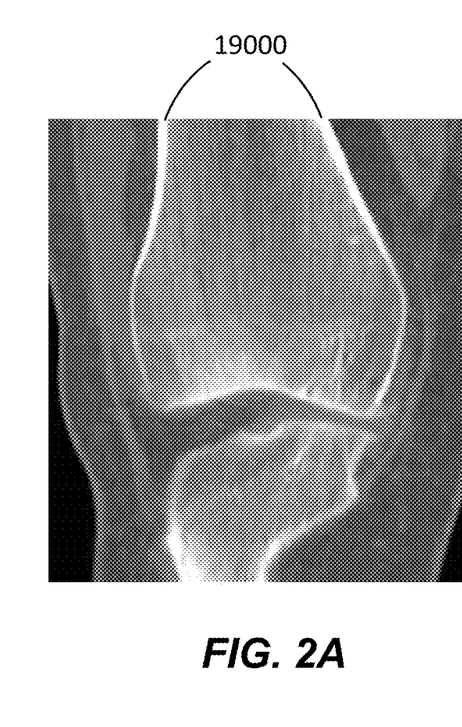
FIG. 2a depicts exemplary image data from which edges of a patient's femur and tibia may be identified.

Then, the image data can be analyzed or segmented 930 to identify those data corresponding to a particular biological feature of interest. For example, as shown in FIG. 2A, image data can be used to identify the edges of a biological structure, in this case, the surface outline for each of the patient's femur and tibia. As shown, the distinctive transition in color intensity or grayscale 19000 at the surface of the structure can be used to identify pixels, voxels, corresponding data points, a continuous line, and/or surface data representing the surface or other feature of the biological structure. This step can be performed automatically (for example, by a computer program operator function) or manually (for example, by a clinician or technician), or by a combination of the two.

Figure 2B:
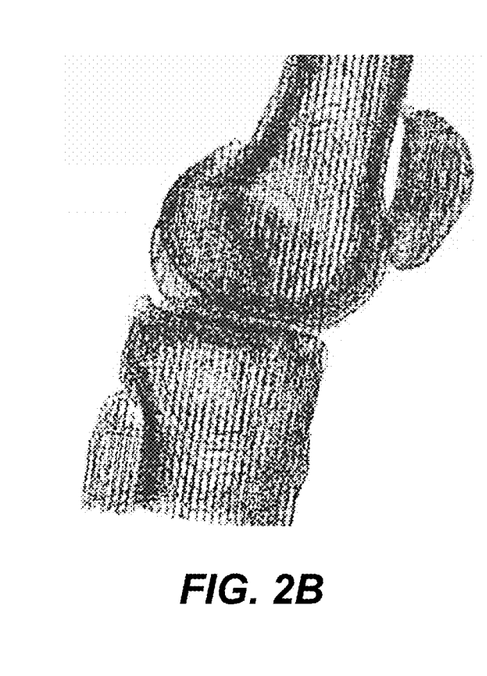
FIG. 2b depicts a 3D representation of the biological structure of a patient's knee joint created from segmented and selected data from multiple images.

Optionally, the segmented data can be combined 940. For example, in a single image, segmented and selected reference points (e.g., derived from pixels or voxels) and/or other data can be combined to create one or more lines representing the surface outline of a biological structure. Moreover, as shown in FIG. 2B, the segmented and selected data from multiple images can be combined to create a 3D representation of the biological structure. Alternatively, the images can be combined to form a 3D data set, from which the 3D representation of the biological structure can be derived directly using a 3D segmentation technique, for example an active surface or active shape model algorithm or other model based or surface fitting algorithm.

Optionally, the 3D representation of the biological structure can be generated, manipulated, smoothed and/or corrected, for example, by employing a 3D polygon surface, a subdivision surface or parametric surface such as, for example, a non-uniform rational B-spline (NURBS) surface. For a description of various parametric surface representations see, for example Foley, J. D. et al., Computer Graphics: Principles and Practice in C; Addison-Wesley, 2nd edition (1995). Various methods are available for creating a parametric surface. In various embodiments, the 3D representation can be converted directly into a parametric surface by connecting data points to create a surface of polygons and applying rules for polygon curvatures, surface curvatures, and other features. Alternatively, a parametric surface can be best-fit to the 3D representation, for example, using publicly available software such as Geomagic® software (Research Triangle Park, N.C.).

Then, the data can be presented as part of a model 950, for example, a patient-specific virtual model that includes the biological feature(s) of interest. The data can be utilized to create multiple models, representing different anatomical features (i.e., individual models representing bone surfaces, bone structure variations or interfaces, articulating surfaces, muscles and/or connective tissues, the patient's skin surface, etc.) or a single model can incorporate multiple features of interest.

As will be appreciated by those of skill in the art, one or more of these steps 910, 930, 940, 950 can be repeated 911, 931, 941, 951 as often as desired to achieve the desired result. Moreover, the steps can be repeated reiteratively 932, 933, 934. If desired, the practitioner can proceed directly 933 from the step of segmenting image data 930 to presenting the data as part of a model 950.

In various embodiments, individual images of a patient's biological structure can be segmented individually and then, in a later step, the segmentation data from each image can be combined. The images that are segmented individually can be one of a series of images, for example, a series of coronal tomographic slices (e.g., front to back) and/or a series of sagittal tomographic slices (e.g., side to side) and/or a series of axial tomographic slices (e.g., top to bottom) of the patient's joint. In some cases, segmenting each image individually can create noise in the combined segmented data. As an illustrative example, in an independent segmentation process, an alteration in the segmentation of a single image may not alter the segmentation in contiguous images in a series. Accordingly, an individual image can be segmented to show data that appears discontinuous with data from contiguous images. To address this issue, certain embodiments include methods for generating a model from a collection of images, for example, simultaneously, rather than from individually segmented images. One such method is referred to as deformable segmentation, as described in, for example, U.S. Patent Publication No. 2012-0209394.

In various embodiments, information collected from a patient or patient group, including the image data and/or models described herein, can include points, surfaces, and/or landmarks, collectively referred to herein as "reference points." In certain embodiments, the reference points can be selected and used to derive a varied or altered surface, such as, without limitation, an ideal surface or structure.

In various embodiments, reference points can be used to create a model of the patient's relevant biological feature(s) and/or one or more patient-adapted surgical steps, tools, and implant components. For example the reference points can be used to design a patient-adapted implant component having at least one patient-specific or patient-engineered feature, such as a surface, dimension, or other feature.

Sets of reference points can be grouped to form reference structures used to create a model of a joint, an implant design, and/or a tool design. Designed implant and/or tool surfaces can be derived from single reference points, triangles, polygons, or more complex surfaces, such as parametric or subdivision surfaces, or models of joint material, such as, for example, articular cartilage, subchondral bone, cortical bone, endosteal bone or bone marrow. Various reference points and reference structures can be selected and manipulated to derive a varied or altered surface, such as, without limitation, an ideal surface or structure.

The reference points can be located on or in the joint that will receive the patient-adapted implant. For example, the reference points can include weight-bearing surfaces or locations in or on the joint, a cortex in the joint, cortical and/or cancellous wall boundaries, and/or an endosteal surface of the joint. The reference points also can include surfaces or locations outside of but related to the joint. Specifically, reference points can include surfaces or locations functionally related to the joint.

For example, in embodiments directed to the knee joint, reference points can include one or more locations ranging from the hip down to the ankle or foot. The reference points also can include surfaces or locations homologous to the joint receiving the implant. For example, in embodiments directed to a knee, a hip, or a shoulder joint, reference points can include one or more surfaces or locations from the contralateral knee, hip, or shoulder joint.

Reference points and/or data for obtaining measurements of a patient's joint, for example, relative-position measurements, length or distance measurements, curvature measurements, surface contour measurements, thickness measurements (in one location or across a surface), volume measurements (filled or empty volume), density measurements, and other measurements, can be obtained using any suitable technique. For example, one dimensional, two-dimensional, and/or three-dimensional measurements can be obtained using data collected from mechanical means, laser devices, electromagnetic or optical tracking systems, molds, materials applied to the articular surface that harden as a negative match of the surface contour, and/or one or more imaging techniques described above herein and/or known in the art. Data and measurements can be obtained non-invasively and/or preoperatively. Alternatively, measurements can be obtained intraoperatively, for example, using a probe or other surgical device during surgery.

In certain embodiments, imaging data collected from the patient, for example, imaging data from one or more of x-ray imaging, digital tomosynthesis, cone beam CT, non-spiral or spiral CT, non-isotropic or isotropic MRI, SPECT, PET, ultrasound, laser imaging, and/or photo-acoustic imaging is used to qualitatively and/or quantitatively measure one or more of a patient's biological features, one or more of normal cartilage, diseased cartilage, a cartilage defect, an area of denuded cartilage, subchondral bone, cortical bone, endosteal bone, bone marrow, a ligament, a ligament attachment or origin, menisci, labrum, a joint capsule, articular structures, and/or voids or spaces between or within any of these structures. The qualitatively and/or quantitatively measured biological features can include, but are not limited to, one or more of length, width, height, depth and/or thickness; curvature, for example, curvature in two dimensions (e.g., curvature in or projected onto a plane), curvature in three dimensions, and/or a radius or radii of curvature; shape, for example, two-dimensional shape or three-dimensional shape; area, for example, surface area and/or surface contour; perimeter shape; and/or volume of, for example, the patient's cartilage, bone (subchondral bone, cortical bone, endosteal bone, and/or other bone), ligament, and/or voids or spaces between them. In certain embodiments, measurements of biological features can include any one or more of the illustrative measurements identified in U.S. Patent Publication No. 2012-0209394. Additional patient-specific measurements and information that can be used in the evaluation can include, for example, joint kinematic measurements, bone density measurements, bone porosity measurements, soft and connective tissues structures, skin, muscles, identification of damaged or deformed tissues or structures, and patient information, such as patient age, weight, gender, ethnicity, activity level, and overall health status. Moreover, the patient-specific measurements may be compared, analyzed or otherwise modified based on one or more "normalized" patient model or models, or by reference to a desired database of anatomical features of interest. For example, a series of patient-specific femoral measurements may be compiled and compared to one or more exemplary femoral or tibial measurements from a library or other database of "normal" (or other reference population) femur measurements. Comparisons and analysis thereof may concern, but is not limited to, one or more or any combination of the following dimensions: femoral shape, length, width, height, of one or both condyles, intercondylar shapes and dimensions, trochlea shape and dimensions, coronal curvature, sagittal curvature, cortical/cancellous bone volume and/or quality, etc., and a series of recommendations and/or modifications may be accomplished. Any parameter mentioned throughout the specification, including anatomic, biomechanical and kinematic parameters, can be utilized, not only in the knee, but also in the hip, shoulder, ankle, elbow, wrist, spine and other joints. Such analysis may include modification of one or more patient-specific features and/or design criteria for the implant to account for any underlying deformity reflected in the patient-specific measurements. If desired, the modified data may then be utilized to select and/or design an appropriate implant and/or tool to match the modified features, and a final verification operation may be accomplished to ensure the selected and/or designed implant and/or tool is acceptable and appropriate to the original unmodified patient-specific measurements (i.e., the selected and/or designed implant and/or tool will ultimately "fit" the original patient anatomy). In alternative embodiments, the various anatomical features may be differently "weighted" during the comparison process (utilizing various formulaic weightings and/or mathematical algorithms), based on their relative importance or other criteria chosen by the designer/programmer and/or physician.

In one exemplary embodiment, the various anatomical features of the tibia (i.e., anterior-posterior and/or medial-lateral dimensions, perimeters, medial/lateral slope, shape, tibial spine height, and other features) could be measured, modeled, and then compared to and/or modified based on a database of one or more "normal" or "healthy" tibial measurements and/or models, with the resulting information used to identify anatomical deformities and/or used to select and/or design a desired implant shape, size and placement. If desired, similar verification of implant appropriateness to the original measured parameters may be accomplished as well. In various embodiments, the various anatomical features of any joint can be measured and then compared/modified based on a database of "healthy" or otherwise appropriate measurements of appropriate joints, including those of a medial condyle, a lateral condyle, a trochlea, a medial tibia, a lateral tibia, an entire tibia, a medial patella, a lateral patella, an entire patella, a medial trochlea, a central trochlea, a lateral trochlea, a portion of a femoral head, an entire femoral head, a portion of an acetabulum, an entire acetabulum, a portion of a glenoid, an entire glenoid, a portion of a humeral head, an entire humeral head, a portion of an ankle joint, an entire ankle joint and/or a portion or an entire elbow, wrist, hand, finger, spine, or facet joint.

In addition to (or optionally in place of) the above-mentioned measurements, it may be desirable to obtain measurements of the targeted joint (as well as surrounding anatomical areas and/or other joints of the patient's anatomy) in a weight-bearing condition. Such measurements can provide data on the alignment and/or movement of the joint and surrounding structures (as well as the loading conditions of the various joint components)—information which may be difficult to obtain or model from standard imaging techniques (i.e., sitting or lying X-rays, CT-scans and/or MRI imaging). Such load-bearing measurements can include imaging of the patient standing, kneeling, walking and/or carrying loads of varying sizes and/or weights.

Figure 3:
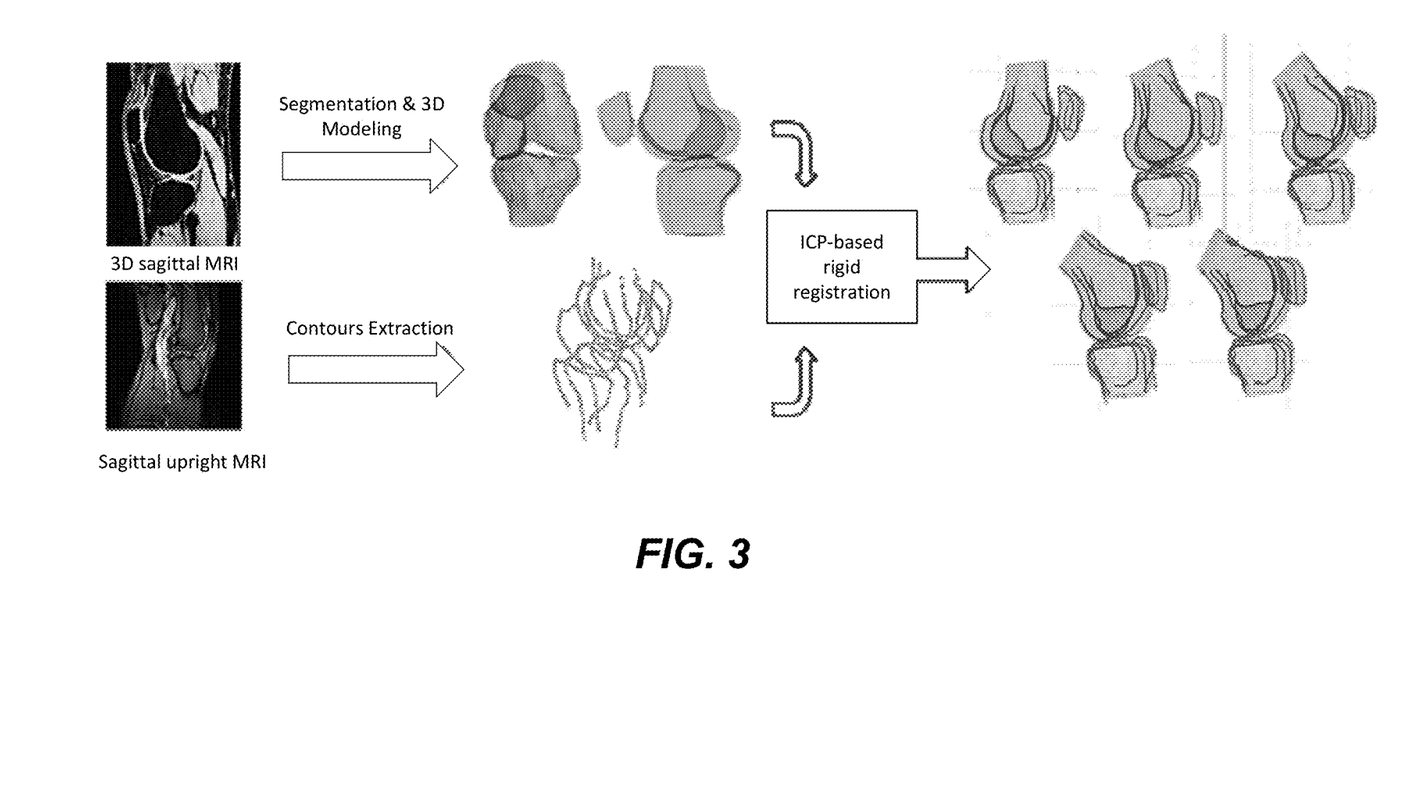
FIG. 3 is a flowchart illustrating exemplary steps for a process to acquire and model weight-bearing kinematic information regarding a joint.

For example, in some embodiments, knee kinematics under physiological full weight-bearing condition, including the influence of gravitational forces, may be obtained using registration of high resolution static MRI data from a supine acquisition with low resolution data of loaded flexion positions (quasi-static upright MRI data) from a standing acquisition. FIG. 3 shows an overview of such a method. Additionally or alternatively, in some embodiments, data of loaded flexion positions can be obtained by real-time MRI scanning of a knee joint during various flexion and/or extension movements, such as, for example, those discussed below. Furthermore, in some embodiments, one or more imaging protocols may be optimized to collect muscle activity of one or more muscles throughout such flexion and/or extension movements.

In some embodiments, high resolution MRI data can be acquired using, for example, a 1.5T Philips Intera system and quasi-static MRI data (full body weight bearing) can be obtained with, for example, a 0.6T Fonar Upright™ system. Table 1, below, provides exemplary scan parameters. Contours of physiological features of interest (e.g., femur, tibia, and patella) from both MRI techniques can be extracted using manual or automated segmentation. And anatomical surface models can then be obtained for the high resolution static data.

TABLE 1

Exemplary scan parameters for weight-bearing kinematic assessment.

| | Static MRI | Dynamic Upright MRI |
|---|---|---|
| Scanner | Philips, Intera, 1.5 T | Upright ™ MRI, Fonar, 0.6 T |
| MRI sequence | 3 D FS T1-FFE | 2 D steady state GE |
| Scan planes | sagittal | sagittal |
| TR (msec) | 60 | 143 |
| TE (msec) | 5 | 17 |
| Flip angle (°) | 40 | 30 |
| Pixel spacing (mm) | 0.27 × 0.27 | 0.54 × 0.54 |
| Slice thickness (mm) | 3 | 4 |
| Slice gap (mm) | 1.5 | 15 |
| Matrix | 512 × 512 | 480 × 480 |
| FOV (mm) | 140 | 259 |
| Scan time (min) | <15 | <27 |

Figure 4:
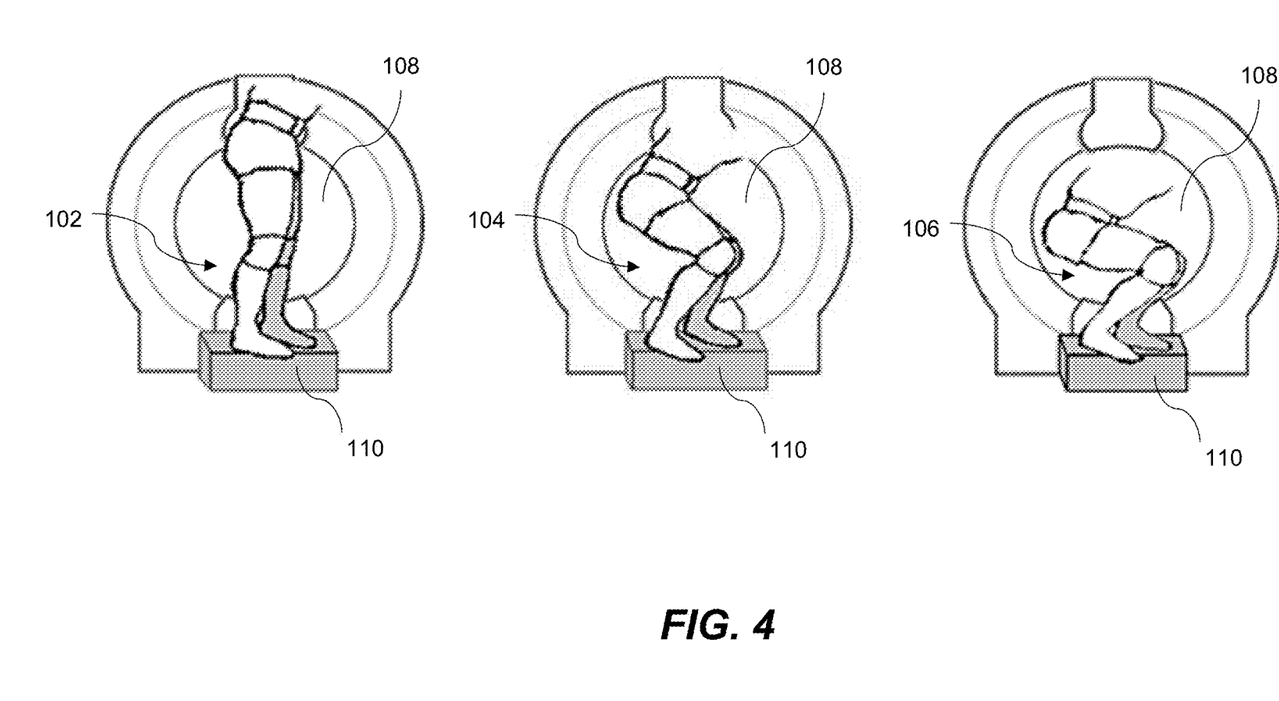
FIG. 4 depicts three exemplary positionings of a patient for acquiring imaging information regarding a knee joint at three different flexion angles, respectively.

In some embodiments, upright MRI acquisition can consist of Multi-2D quasi-static scans each including 4 slices for each flexion angle. Scans may be acquired in the sagittal plane to allow simultaneous capture of femur, tibia and patella. To facilitate 3D position measurement and registration, 2 of the 4 slices may be adjusted such that the patella is included. FIG. 4 shows a schematic illustration of subject stance and corresponding knee flexion in a first 102, second 104, and third 106 flexion position, relative to an imaging device 108 (e.g., upright MRI system) and a supporting surface 110 (e.g., elevatable table). Starting with full knee extension, the subjects may increase the flexion in 4-5 steps to reach the maximum flexion angle possible under space (and force) limitations due to the sizes of the subject tight and knee coil. Knees may be softly padded for stabilization in lateral-medial direction in order to reduce motion artifacts. Subjects may also be instructed to transfer bodyweight onto the leg being imaged and maintain the predefined flexion position in single-legged stance during the acquisition of the 4 sagittal slices. MR acquisition at every flexion angle may last for approximately 39 seconds. All acquisitions may be obtained near the scanner isocenter.

In some embodiments, 3D anatomical models for all three knee bones (femur, patella, and tibia) can also obtained from segmentation (e.g., manual or automated) of the high-resolution supine MR scans. An isotropic-resampling with linear interpolation can be applied to the original 3D models to obtain high-density models (corresponding meshes hereafter referred to as "original meshes") for further kinematic measurements.

Due to the size of slice thickness, anatomical models reconstructed directly after manual tracing of structures' contours normally show obvious steps between slices. In reality, these anatomical structures are, however, much more regular and smooth. Although inaccuracies in the preparation of high resolution models and low resolution bony outlines (through, e.g., segmentation errors) may be present in each 3D modeling step, such inaccuracies may not have a significant effect on ICP registration outcomes, as discussed below. But, in some embodiments, the number of surface vertices involved in the ICP registration may affect the total registration time for all flexion positions. A 3D model preparation (mesh reduction and smoothing) which facilitates a robust registration in an acceptable registration time may, therefore, be desirable in some embodiments.

Accordingly, some embodiments can optionally include one or more mesh reduction steps. Mesh reduction steps may be performed on the original meshes of the femur, tibia and patella by merging surface vertices within pre-defined merging distances (e.g., 0.25, 0.50, 0.75, 1.00, 1.25 or 1.50 mm). For example, in some embodiments, a mesh reduction step may be performed on the original mesh by merging surface vertices within about 0.5 mm. One or more mesh reduction steps may be followed by a non-shrinkage smoothing step using the Taubin smoothing algorithm45 to reduce the stepping and bumping effects, resulting in a reduced mesh. In some cases, a mesh reduction with a 0.5 mm merging distance and a non-shrinkage Taubin smoothing may be optimum for achieving robust registration in an acceptable registration time. For example, mesh reduction with a 0.5 mm merging distance and a non-shrinkage Taubin smoothing may produce reduced meshes with less than 0.25 mm deviation (Root Mean Squared Distance for all vertices) compared to the corresponding original meshes and may also provide a very small to negligible overall effect on registration (e.g., less than 0.5 mm deviation in one or more translation components, less than 0.25 mm deviation in rotation axis, and less than 0.1° deviation in rotation angle) and allow an overall registration time under 100 seconds for all knee components.

Figure 5:
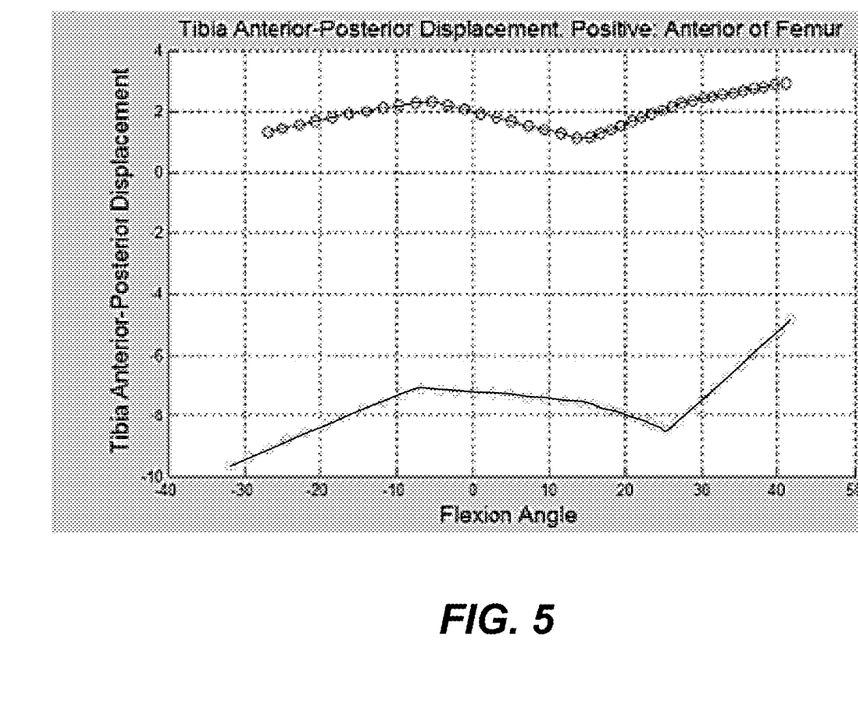
FIG. 5 is a graph of exemplary kinematic data regarding the displacement of the femur relative to the tibia during flexion obtained utilizing the process of FIG. 3.
Figure 6:
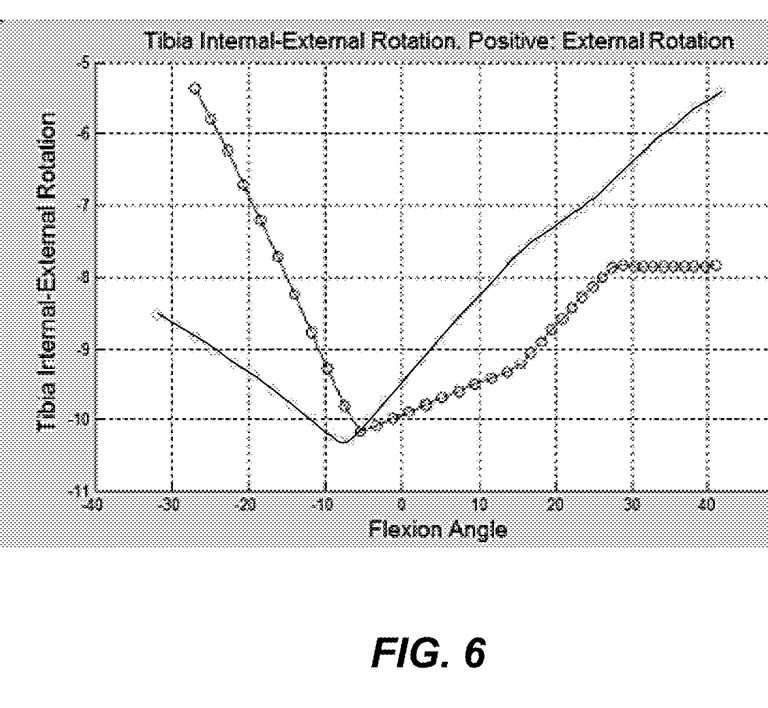
FIG. 6 is a graph of exemplary kinematic data regarding internal-external rotation of the femur relative to the tibia during flexion obtained utilizing the process of FIG. 3.

In some embodiments, after upright MRI acquisition, anatomical models of the static data (original and/or reduced meshes) may each be registered to corresponding low resolution contours from the weight-bearing scans using an iterative closest point (ICP) based approach. A reference registration step can be carried out to register the anatomical models to the full extension loaded position. Rotation matrices and translation vectors describing the movement of each 3D model to its registered alignment in the full extension contours (first static acquisition) can be recorded and used as initial conditions for ICP registration between full extension and first flexion acquisition. This technique can then be repeated to facilitate ICP registrations between subsequent flexion acquisitions. The high resolution 3D models of femur, tibia and patella can be separately registered with their corresponding contours in the movement data to allow tracking and kinematic evaluation of individual knee components. Data obtained from this process can then be used for desired kinematic calculations (e.g., tibio-femoral kinematics, patella-femoral kinematics). For example, FIGS. 5 and 6 illustrate sample tibio-femoral kinematic calculations for two exemplary subjects. These exemplary calculations were carried out using the joint coordinate system, as described by Grood E S, et al. (J Biomech, 105:136-144, 1994, which is incorporated herein by reference in its entirety), with its corresponding femur and tibia anatomical landmarks. The weight-bearing data and kinematic information may be used, for example, to modify and/or evaluate biomechanical models (e.g., as described below) and/or optimize parameters of patient-adapted articular repair systems, as discussed herein.

In some embodiments, for determination of the mechanical leg axis and/or lower limb alignment, the centers of the femoral head, the knee joint center and ankle joint center can be identified on a single coronal MR image. Additionally or alternatively, a multi-station imaging protocol (e.g., as specified in Table 2 below), which involves acquisitions around hip, knee, and ankle joints, can be used. For analysis of the mechanical leg axis and measurement of HKA-angle, both coronal and axial slices may be acquired around femoral head and neck, knee and ankle joint in a weight-bearing bi-pedal stance. Axial slices may be acquired to allow later torsion measurements and correction of femur and tibia. This can be accomplished with setup that involves the positioning of a different coil around the hip, the knee, and the ankle, respectively, prior to image acquisition. In some instances, this may considerably reduce movement artifacts (e.g., relative to movement artifacts in a coil-interchanging approach). The SNR may be optimized by the right-angle relationship between the axis of the solenoid receiver coils and the horizontal direction of the magnetic field. In some embodiments, the image acquisition may start around the hip joint. Knee and ankle acquisitions may subsequently be obtained after corresponding table elevations. Table elevations for hip, knee and ankle scans may be chosen and registered to ensure optimal image quality near the magnet iso-center. A dedicated bi-planar (e.g., coronal/axial) image-based approach may be utilized for the determination of the three joint centers. The registration between all MR acquisitions may be established using information on table elevation and image position and orientation contained in the DICOM header file. After this registration, the centers of the femoral head, knee, and ankle joints can be determined on coronal view and fine-tuned with the help of the orthogonal axial view. Accordingly, such a method can be used to measure loaded leg axis (e.g., mechanical, anatomical) in clinically applicable scan time (e.g., less than 22 min) and without the need of coil replacement.

limited to the patient's age, gender, weight, height, size, body mass index, and race. Desired limb alignment and/or deformity correction can be added into the model. The position of bone cuts on one or more articular surfaces as well as the intended location of implant bearing surfaces on one or more articular surfaces can be entered into the model.

A patient-specific biomotion model can be derived that includes combinations of parameters discussed above. The biomotion model can simulate various activities of daily life, including normal gait, stair climbing, descending stairs, running, kneeling, squatting, sitting and any other physical activity (including activities relevant to other joints of interest). The biomotion model can start out with standardized activities, typically derived from reference databases. These reference databases can be generated, for example, using biomotion measurements using force plates and motion trackers using radiofrequency or optical markers and video equipment.

The biomotion model can then be individualized with use of patient-specific information including at least one of, but not limited to, the patient's age, gender, weight, height, body mass index, and race, the desired limb alignment or deformity correction, and the patient's imaging data, for example, a series of two-dimensional images or a three-dimensional representation of the joint for which surgery is contemplated.

An implant shape including associated bone cuts generated in various optimizations and/or modifications discussed herein, for example, limb alignment, deformity correction

TABLE 2

Exemplary scan parameters for upright-MRI-based determination of leg mechanical axis.

| | Hip axial | Hip coronal | Knee axial | Knee coronal | Ankle axial | Ankle coronal |
|---|---|---|---|---|---|---|
| Pulse sequence | T2 - FSE | T2 - FSE | T2 - FSE | T2 - FSE | T2 - FSE | T2 - FSE |
| Number of Slices | 10 | 7 | 10 | 7 | 7 | 7 |
| TR (msec) | 1645 | 1603 | 1645 | 2300 | 2300 | 2300 |
| TE (msec) | 160 | 100 | 160 | 160 | 160 | 160 |
| Flip angle (°) | 90 | 90 | 90 | 90 | 90 | 90 |
| Pixel spacing (mm) | 1.56 × 1.56 | 0.78 × 0.78 | 0.93 × 0.93 | 0.78 × 0.78 | 0.93 × 0.93 | 1.56 × 1.56 |
| Slice thickness (mm) | 6 | 8 | 6 | 6 | 6 | 7 |
| Slice gap (mm) | 9 | 10 | 9 | 7 | 8 | 8 |
| Matrix | 256 × 256 | 512 × 512 | 256 × 256 | 512 × 512 | 256 × 256 | 256 × 256 |
| FOV (mm) | 40 | 40 | 24 | 40 | 24 | 40 |
| Scan time (sec) | 79 | 52 | 72 | 55 | 55 | 55 |

In certain embodiments, a computer program simulating biomotion of one or more joints, such as, for example, a knee joint, or a knee and ankle joint, or a hip, knee and/or ankle joint, can be utilized. In certain embodiments, imaging data as previously described, which can include information related to the joint or extremity of interest as well as information regarding adjacent anatomical structures, can be entered into the computer program. In addition to (or in place of) patient-specific image data, patient-specific kinematic data, for example obtained as described above, can be entered into the computer program. Alternatively, patient-specific navigation data, for example generated using a surgical navigation system, image guided or non-image guided, can be entered into the computer program. This kinematic or navigation data can, for example, be generated by applying optical or RF markers to the limb and by registering the markers and then measuring limb movements, for example, flexion, extension, abduction, adduction, rotation, and other limb movements.

Optionally, other data including anthropometric data may be added for each patient. These data can include but are not and/or bone preservation on one or more articular surfaces, can be introduced into the model. Table 3 includes an exemplary list of parameters that can be measured in a patient-specific biomotion model.

TABLE 3

Parameters measured in a patient-specific biomotion model.

| Joint implant | Measured Parameter |
|---|---|
| knee | Medial femoral rollback during flexion |
| knee | Lateral femoral rollback during flexion |
| knee | Patellar position, medial, lateral, superior, inferior for different flexion and extension angles |
| knee | Internal and external rotation of one or more femoral condyles |
| knee | Internal and external rotation of the tibia |
| knee | Flexion and extension angles of one or more articular surfaces |
| knee | Anterior slide and posterior slide of at least one of the medial and lateral femoral condyles during flexion or extension |
| knee | Medial and lateral laxity throughout the range of motion |

TABLE 3-continued

Parameters measured in a patient-specific biomotion model.

| Joint implant | Measured Parameter |
|---|---|
| knee | Contact pressure or forces on at least one or more articular surfaces, e.g., a femoral condyle and a tibial plateau, a trochlea and a patella |
| knee | Contact area on at least one or more articular surfaces, e.g., a femoral condyle and a tibial plateau, a trochlea and a patella |
| knee | Forces between the bone-facing surface of the implant, an optional cement interface and the adjacent bone or bone marrow, measured at least one or multiple bone cut or bone-facing surface of the implant on at least one or multiple articular surfaces or implant components. |
| knee | Ligament location, e.g., ACL, PCL, MCL, LCL, retinacula, joint capsule, estimated or derived, for example using an imaging test. |
| knee | Ligament tension, strain, shear force, estimated failure forces, loads for example for different angles of flexion, extension, rotation, abduction, adduction with the different positions or movements optionally simulated in a virtual environment. |
| knee | Potential implant impingement on other articular structures, e.g., in high flexion, high extension, internal or external rotation, abduction or adduction or any combinations thereof or other angles/positions/movements. |

The above list is not meant to be exhaustive, but only exemplary. Any other biomechanical parameter known in the art can be included in the analysis.

The information from the measurements and/or models described above can then be utilized (alone or in combination with other data described herein) to design various features of a joint repair system. The implant and/or procedure design may be optimized with the objective to establish normal or near normal kinematics. The implant optimizations can include one or multiple implant components. Implant and/or procedure optimizations based on patient-specific data include (but are not limited to):

Changes to external, joint-facing implant shape in coronal plane

Changes to external, joint-facing implant shape in sagittal plane

Changes to external, joint-facing implant shape in axial plane

Changes to external, joint-facing implant shape in multiple planes or three dimensions Changes to internal, bone-facing implant shape in coronal plane Changes to internal, bone-facing implant shape in sagittal plane Changes to internal, bone-facing implant shape in axial plane Changes to internal, bone-facing implant shape in multiple planes or three dimensions Changes to one or more bone cuts, for example with regard to depth of cut, orientation of cut, joint-line location, and/or joint gap width When changes are made on multiple articular surfaces or implant components, these can be made in reference to or linked to each other. For example, in the knee, a change made to a femoral bone cut based on patient-specific data can be referenced to or linked with a concomitant change to a bone cut on an opposing tibial surface, for example, if less femoral bone is resected, more tibial bone may be resected.

What is claimed is:

1. A method of making an implant component for a knee joint of a patient, the method comprising:
receiving first imaging data associated with the knee joint, wherein the first imaging data comprises imaging data associated with the knee joint when the patient is in a single-legged stance and the knee joint is under physiological full weight-bearing condition;
receiving second imaging data associated with the knee joint, wherein the second imaging data comprises imaging data obtained at a higher resolution than a resolution at which the first imaging data was obtained;
generating one or more contours from the first imaging data;
generating one or more anatomic models from the second imaging data;
registering each of the one or more anatomic models from the second imaging data to one or more corresponding contours from the first imaging data;
deriving kinematic information regarding the knee joint based, at least in part, on the one or more registered anatomic models; and
designing an implant component based, at least in part, on the derived kinematic information regarding the joint.

2. The method of claim 1, wherein first and/or second imaging data comprises MRI imaging data.

3. The method of claim 1, wherein the registering comprises employing an iterative closest point based process.

4. The method of claim 1, wherein the first imaging data includes imaging data acquired from four different planes through the knee joint.

5. The method of claim 1, wherein the first imaging data comprises imaging data of the knee joint in the sagittal plane.

6. A method of making an implant component for a knee joint of a patient, the method comprising:
receiving first imaging data associated with the knee joint, wherein the first imaging data comprises imaging data associated with the knee joint when the knee joint is in at least one weight-bearing position;
receiving second imaging data associated with the knee joint, wherein the second imaging data comprises imaging data obtained at a higher resolution than a resolution at which the first imaging data was obtained;
generating one or more contours from the first imaging data;
generating one or more anatomic models from the second imaging data;
registering each of the one or more anatomic models from the second imaging data to one or more corresponding contours from the first imaging data;
deriving kinematic information regarding the knee joint based, at least in part, on the one or more registered anatomic models; and
designing an implant component based, at least in part, on the derived kinematic information regarding the joint, wherein the first imaging data further comprises imaging data associated with the knee joint when the knee joint is in a first weight-bearing position, in a second weight-bearing position, in a third weight-bearing position, and in a fourth weight-bearing position.

7. The method of claim 6, wherein the first weight-bearing position comprises the knee joint being positioned in full extension; the second weight-bearing position comprises the knee joint being positioned in flexion at a first flexion angle; the third weight-bearing position comprises the knee joint being positioned in flexion at a second flexion angle, the second flexion angle being greater than the first; and the fourth weight-bearing position comprises the knee joint being positioned in flexion at a third flexion angle, the third flexion angle being greater than the second.

8. The method of claim 6, wherein the registering further comprises:
generating first registered models by registering each of the one or more anatomic models from the second imaging data to one or more corresponding contours generated from the imaging data associated with the knee joint in the first weight-bearing position;
generating second registered models by registering the first registered models to corresponding contours generated from the imaging data associated with the knee joint in the second weight-bearing position;
generating third registered models by registering the second registered models to corresponding contours generated from the imaging data associated with the knee joint in the third weight-bearing position; and generating fourth registered models by registering the third registered models to corresponding contours generated from the imaging data associated with the knee joint in the fourth weight-bearing position.

9. A method of making a surgical repair system for a knee joint of a patient, the method comprising:
receiving first imaging data associated with the knee joint, wherein the first imaging data comprises imaging data associated with the knee joint when the patient is in a single-legged stance and the knee joint is under physiological full weight-bearing condition;
receiving second imaging data associated with the knee joint, wherein the second imaging data comprises imaging data obtained at a higher resolution than a resolution at which the first imaging data was obtained;
generating one or more contours from the first imaging data;
generating one or more anatomic models from the second imaging data;
registering each of the one or more anatomic models to one or more corresponding contours from the first imaging data;
deriving kinematic information regarding the knee joint based, at least in part, on the one or more registered anatomic models;
designing an implant component based, at least in part, on the derived kinematic information regarding the joint; and
designing a surgical tool based, at least in part, on the derived kinematic information regarding the joint.

10. The method of claim 9, wherein first and/or second imaging data comprises MRI imaging data.

11. The method of claim 9, wherein the registering comprises employing an iterative closest point based process.

12. A method of making a surgical repair system for a knee joint of a patient, the method comprising:
receiving first imaging data associated with the knee joint, wherein the first imaging data comprises imaging data associated with the knee joint when the knee joint is in at least one weight-bearing position;
receiving second imaging data associated with the knee joint, wherein the second imaging data comprises imaging data obtained at a higher resolution than a resolution at which the first imaging data was obtained;
generating one or more contours from the first imaging data;
generating one or more anatomic models from the second imaging data;
registering each of the one or more anatomic models to one or more corresponding contours from the first imaging data;
deriving kinematic information regarding the knee joint based, at least in part, on the one or more registered anatomic models;
designing an implant component based, at least in part, on the derived kinematic information regarding the joint; and
designing a surgical tool based, at least in part, on the derived kinematic information regarding the joint, wherein the first imaging data further comprises imaging data associated with the knee joint when the knee joint is in a first weight-bearing position, in a second weight-bearing position, in a third weight-bearing position, and in a fourth weight-bearing position.

13. The method of claim 12, wherein the first weight-bearing position comprises the knee joint being positioned in full extension; the second weight-bearing position comprises the knee joint being positioned in flexion at a first flexion angle; the third weight-bearing position comprises the knee joint being positioned in flexion at a second flexion angle, the second flexion angle being greater than the first; and the fourth weight-bearing position comprises the knee joint being positioned in flexion at a third flexion angle, the third flexion angle being greater than the second.

14. The method of claim 12, wherein the registering further comprises:
generating first registered models by registering each of the one or more anatomic models from the second imaging data to one or more corresponding contours generated from the imaging data associated with the knee joint in the first weight-bearing position;
generating second registered models by registering the first registered models to corresponding contours generated from the imaging data associated with the knee joint in the second weight-bearing position;
generating third registered models by registering the second registered models to corresponding contours generated from the imaging data associated with the knee joint in the third weight-bearing position; and
generating fourth registered models by registering the third registered models to corresponding contours generated from the imaging data associated with the knee joint in the fourth weight-bearing position.

* * * * *